(12) United States Patent
Hori et al.

(10) Patent No.: US 6,521,600 B1
(45) Date of Patent: Feb. 18, 2003

(54) COMPOUND, WF002, PRODUCTION THEREOF AND USE THEREOF

(75) Inventors: Yasuhiro Hori, Tokyo (JP); Masami Ezaki, Tsukuba (JP); Yasuhisa Tsurumi, Tsukuba (JP); Shigehiro Takase, Ishioka (JP); Motohiro Hino, Tsuchiura (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/720,331

(22) PCT Filed: Jun. 16, 1999

(86) PCT No.: PCT/JP99/03191

§ 371 (c)(1),
(2), (4) Date: Jan. 18, 2001

(87) PCT Pub. No.: WO99/67272

PCT Pub. Date: Dec. 29, 1999

(30) Foreign Application Priority Data

Jun. 23, 1998 (AU) ................................................ PP4293

(51) Int. Cl.$^7$ .................... A61K 31/7028; C07H 15/24; C12N 1/00; C12P 19/44; C12P 19/60
(52) U.S. Cl. ........................... 514/27; 536/6.1; 435/52; 435/74; 435/75; 435/254.1; 435/911
(58) Field of Search ............................. 514/27; 536/6.1; 435/254.1, 74, 75, 52, 911

(56) References Cited

PUBLICATIONS

P. J. Houghton, et al., Pharmaceutical Pharmacological Letters, vol. 7, pp. 96–98, "Antimicrobial Activity of Extracts of Some Bignoniaceae From Malaysia", 1997.
N. Akhtar, et al., Chemical Abstracts, vol. 121, No. 22, p. 557, AN 263400, XP–002115071, "Rubrinol, A New Antibacterial Triterpenoid From Plumeria Rubra", Nov. 28, 1994.
D. K. Verma, et al., Indian Drugs, vol. 34, No. 7, pp. 390–392, "Antimicrobial Active Triterpenoids From Lantana Species", 1997.
S. C. Hess, et al., Chemical Abstracts, vol. 123, No. 25, p. 34, AN 329308, XP–002115072, "Antibacterial Activity and Phytochemical Analysis of Vochysia Divergens (Vochysiaceae)", Dec. 18, 1995.
G. Turhan, et al., Journal of Phytopathology, vol. 140, No. 2, pp. 97–113, "Antagonistic Activity of Five Myrothecium Species Against Fungi and Bacteria In Vitro", 1994.

*Primary Examiner*—James O. Wilson
*Assistant Examiner*—Everett White
(74) *Attorney, Agent, or Firm*—Oblon, Spivak, McClelland, Maier & Neustadt, P.C.

(57) ABSTRACT

The present invention provides a new bioactive compound of formula (I), which has an antimicrobial activity against pathogenic microorganisms, and a process for production thereof. Also provided are a pharmaceutical composition comprising the compound and pharmaceutically acceptable carrier, a use of the WF002 as a medicament and use of the compound for manufacture of the medicament for treatment of infectious disease.

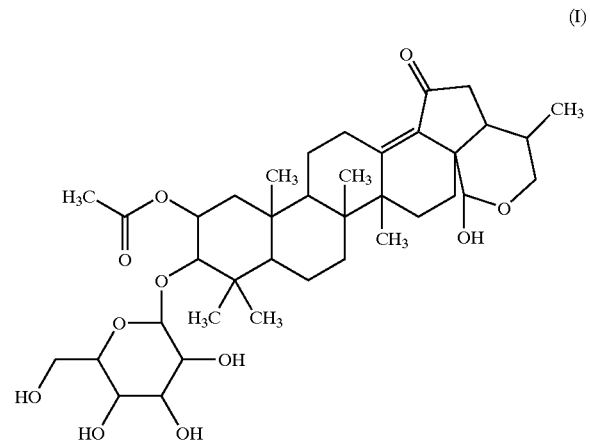

(I)

10 Claims, No Drawings

COMPOUND, WF002, PRODUCTION THEREOF AND USE THEREOF

TECHNICAL FIELD

This invention relates to a new antimicrobial compound. More particularly, it relates to a new antimicrobial compound that has an antimicrobial activity against pathogenic microorganisms, especially pathogenic fungi, to a process for the preparation thereof and to a pharmaceutical composition comprising the same.

DISCLOSURE OF INVENTION

The new compound, WF002 has the following physicochemical properties:

a) Molecular weight: ESI-MS (negative): m/z 689 (M−H)⁻ b) Elemental analysis: C, 61.08; H, 8.83 c) Melting point: 210–211° C.

d) Optical rotation: $[\alpha]_D^{23}$=+58° (c=0.5, methanol)

e) UV absorption spectrum: λ max(ε)=260 nm (methanol, 13000)

f) IR absorption spectrum: ν max(KBr)=3430, 2950, 2880, 1710, 1620, 1450, 1370, 1260, 1100, 1080, 1040 cm⁻¹ g) ¹H-NMR spectrum: (500 MHz, CD₃OD) δ(ppm): 5.11 (1H, m), 4.98 (1H, s), 4.37 (1H, d, J=8 Hz), 4.34 (1H, m), 4.08 (1H, m), 3.86 (1H, m), 3.67 (1H, m), 3.38 (1H, d, J=10 Hz), 3.32 (1H, m), 3.28–3.20 (3H, m), 3.13 (1H, m), 2.58 (1H, m), 2.28 (1H, m), 2.19 (1H, m), 2.06 (3H, s), 2.06–1.95 (3H, m), 1.81–1.50 (7H, m), 1.49–1.20 (4H, m), 1.22 (3H, d, J=8 Hz), 1.20 (3H, s), 1.13 (3H, s), 1.12 (1H, m), 0.98 (3H, s), 0.97 (1H, m), 0.93 (3H, s), 0.92 (3H, s).

h) ¹³C-NMR spectrum: (125 MHz, CD₃OD) δ(ppm): 211.3 (s), 173.2 (s), 157.3 (s), 136.9 (s), 105.9 (d), 95.2 (d), 89.3 (d), 78.3 (d), 77.8 (d), 75.9 (d), 71.9 (d), 71.7 (d), 63.0 (t), 59.4 (t), 56.4 (d), 52.7 (d), 45.94 (d), 45.90 (t), 45.2 (s), 44.9 (s), 44.4 (t), 44.1 (s), 42.1 (s), 39.5 (s), 35.6 (t), 35.0 (t), 31.3 (d), 30.1 (t), 28.7 (q), 28.1 (q), 24.9 (t), 23.0 (t), 21.7 (q), 21.1 (q), 19.4 (q), 19.2 (t), 18.3 (q), 17.9 (q).

i) Solubility
  Soluble: methanol, ethyl acetate, dimethylsulfoxide
  Insoluble: water, n-hexane j) Color reaction
  Positive: reactions with iodine vapor and cerium sulfate, and Molisch's test, respectively.
  Negative: reactions with ninhydrin, Ehrlich's reagent, Dragendorff reagent and ferric chloride, respectively.

k) Nature of substance: Neutral substance l) Thin layer chromatography:
  Carrier: Silica gel 60 F254 (Merck)
  Solvent: dichloromethane:methanol=8:1
  Rf=0.21

From the above physicochemical properties and extensive studies, the provisional chemical structure of WF002 was assigned as follows.

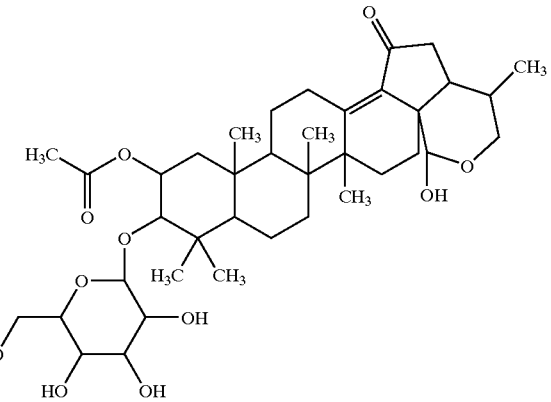

According to this invention, the compound, WF002 can be prepared by culturing a WF002-producing strain, especially belonging to the genus Myrothecium in a nutrient medium.

Particulars of microorganisms used for the production of WF002 and production thereof will be explained in the followings.

Microorganism

The microorganism which can be used for the production of WF002 is a WF002-producing strain belonging to the genus Myrothecium, among which *Myrothecium cinctum* No.002 was newly isolated from a material of Japan.

Lyophilized samples of the newly isolated microorganism, the strain No.002 were deposited with an International Depository Authority on the Budapest Treaty, National Institute of Bioscience and Human-Technology, 1–3, Higashi 1-chome, Tsukuba-shi, Ibaraki-ken, 305-0046 Japan under the deposit number FERM BP-6380 on May 26, 1998.

The fungal strain No.002 was originally isolated from a soil sample. This organism grew rather rapidly on various culture media, and formed orange white to yellowish white colonies. The strain produced many conidial structures on the agar media, while it did not formed teleomorph. The conidial structures consisted of hyphal conidiophores and phialidic conidia, and the conidial masses were dark green to dark gray. On Sabouraud dextrose agar, the strain formed sometimes sporodochial conidiomata. Its mycological characteristics were as follows.

Cultural characteristics on various agar media are summarized in Table 1. Culture on potato dextrose agar grew fairly rapidly, attaining 3.5–4.5 cm in diameter two weeks later at 25° C. This colony surface was plane to raised, felty to cottony, sulcate or wrinkly, exudate, sometimes sectoring, orange white to pale orange at the center and the margin, and gray at the middle. Many conidial structures were formed on the media. The reverse color was pale orange to light orange. Colonies on corn meal agar grew restrictedly, attaining 1.5–2.5 cm in diameter under the same conditions. The surface was plane, thin, sometimes sectoring, white to orange white at the center and the margin, and brownish gray to dark gray at the middle. The reverse was white to orange white. Many conidial structures were formed.

The morphological characteristics were mainly determined from the cultures on a Miura's LCA plate (Mura, K. and M. Kudo: Trans. Mycol. Soc. Japan, 11:116–118, 1970). The conidiophores were erect from vegetative or aerial hyphae. They were semi-macronematous, hyaline, smooth to roughened, repeatedly branched, and formed a whorl of 2–4 phialides at the tips. The phialides were discrete, acrogenous, hyaline, roughened to granulate, cylindrical, with differentiated collarettes, (9–)16–28(–34)×(1.5–)2–3 μm in size, and producing conidia in slimy drops. Conidia were enteroblastic, phialidic, subhyaline to dark green, oblique or longitudinal striate, one-celled, fusiform to lentiform, and 8.5–12×2.5–3.5(–4.5) μm. Vegetative hyphae were smooth, septate, hyaline and branched. The hyphal cells were cylindrical and 1.5–5 μm in width. Chlamydospores were not observed. Sporodochia on Sabouraud dextrose agar were composed of loosely aggregations of hyphae and conidiophores, and 100–300 μm in diameter.

Strain No.002 was able to grow at the temperature range from 6 to 33° C., with the growth optimum at 19 to 22° C. These temperature data were determined on potato dextrose agar (made by NISSUI).

On the basis of comparing the morphological characteristics with fungal taxonomic criteria by von Arx (J. A. von Arx: The Genera of Fungi—Sporulating in Pure Culture. 3rd ed., pp.315, J. Cramer, Vaduz. 1974) and Barron (G. L. Barron: The Genera of Hyphomycetes from Soil. pp.364, Williams & Wilkins, Baltimore, 1968), strain No.002 was considered to belong to the hyphomycete genus Myrothecium Tode (1790). Moreover, above characteristics were corresponded the species description of *Myrothecium cinctum* (Code) Sacc. (1886) by Domsch et al. (K. H. Domsch, W. Gams and T.-H. Anderson: Compendium of Soil Fungi. vol. 1, p.482, Academic Press, London, 1980), with few exceptions. Thus, we identified this isolate as one strain of *Myrothecium cinctum,* and named it *Myrothecium cinctum* No.002.

TABLE 1

Cultural characteristics of strain No.002.

| Media | Cultural characteristics |
|---|---|
| Malt extract agar* | G: Rather restrictedly, 2.5–3.5 cm<br>S: Irregular, plane, felty, formed some conidial structures, yellowish white (2A2) at the center, white to orange white (5A2) at the margin, and olive gray (1F2) at the middle<br>R: Pale yellow (4A3) to grayish yellow (4B3), and olive brown (4E4) at the middle |
| Potato dextrose agar (Difco 0013) | G: Fairly rapidly, 3.5–4.5 cm<br>S: Circular, plane to raised, felty to cottony, sulcate or wrinkly, exudate, sometimes sectoring, formed many conidial structures, orange white (6A2) to pale orange (6A3) at the center and the margin, and gray (1E1) at the middle<br>R: Pale orange (5A3–6A3) to light orange (5A4–6A4) |
| Czapek's solution agar* | G: Rather restrictedly, 2.5–3.5 cm<br>S: Circular, centrally raised to umbonate, zonate, felty, radiately sulcate, exudate, formed few conidial structures, and yellowish white (3A2) to orange white (6A2)<br>R: Pale yellow (4A3) to pale orange (6A3) |
| Sabouraud dextrose agar (Difco 0190) | G: Rather rapidly, 3.0–4.0 cm<br>S: Circular to irregular, centrally raised to umbonate, felty, radiately sulcate or wrinkly, exudate, grayish yellow (4B3) to orange white (6A2), and formed some grayish dots of sporodochia<br>R: Grayish orange (5B5) to brownish orange (5C4) |
| Emerson Yp Ss agar (Difco 0739) | G: Rather rapidly, 3.0–4.0 cm<br>S: Circular, plane, felty, hygroscopic, formed many conidial structures, dark green (27F4–27F5), and orange white (6A2) at the margin<br>R: Light orange (6A4–6A5) |

TABLE 1-continued

Cultural characteristics of strain No.002.

| Media | Cultural characteristics |
|---|---|
| Corn meal agar (Difco 0386) | G: Restrictedly, 1.5–2.5 cm<br>S: Circular, plane, thin, sometimes sectoring, formed many conidial structures, white to orange white (5A2) at the center and the margin, and brownish gray (5F2) to dark gray (1F1) at the middle<br>R: White to orange white (5A2) |
| MY20 agar* | G: Fairly rapidly, 3.5–4.5 cm<br>S: Circular, plane to centrally raised, felty to cottony, exudate, hygroscopic, abundantly formed conidial structures, greenish white (28A2) to greenish gray (28B2) at the center, white to orange white (6A2) at the margin, and dull green (28D4) to dark green (28F4) at the middle<br>R: Olive brown (4E4–4F4), and yellowish white (4A2) at the margin |
| Oatmeal agar (Difco 0552) | G: Spreading broadly, 4.5–5.5 cm<br>S: Circular, plane, felty, radiately sulcate, exudate, hygroscopic, sometimes sectoring, abundantly formed conidial structures, dark gray (1F1) to dark green (27F4), and pale orange (6A3) at the margin |

Abbreviation
G: growth, measuring colony size in diameter, S: colony surface, R: reverse.
*: The compositions of malt extract agar, Czapek's solution agar and MY20 agar were based on JCM Catalogue of Strains (Nakase, T., 6th ed., pp.617, Japan Collection of Microorganisms, the Institute of Physical and Chemical Research, Saitama, 1995).

These characteristics were observed after 14 days of incubation at 25° C. The color descriptions were based on Methuen Handbook of Colour (Kornerup, A. and J. H. Wanscher, 3rd ed., pp.252, Methuen, London, 1978).

It is to be understood that the production of the new compound, WF002 is not limited to the use of the particular organism described herein, which is given for illustrative purpose only. This invention also includes the use of any mutants which are capable of producing the WF002 including natural mutants as well as artificial mutants which can be produced from the described organism by conventional means, such as genetic engineering, X-ray, ultraviolet radiation, treatment with N-methyl-N'-nitro-N-nitrosoguanidine and the like.

Production of WF002

The compound, WF002 can be prepared by culturing a WF002-producing strain in a nutrient medium.

In general, WF002 can be produced by culturing the WF002-producing strain in a nutrient medium containing assimilable sources of carbon and nitrogen, preferably under aerobic conditions (e.g. shaking culture, submerged culture, etc.).

The preferred sources of carbon are carbohydrates such as sucrose, glucose, glycerol, soluble starch and the like.

The preferred sources of nitrogen are cottonseed meal, soybean flour, yeast extract, peptone, gluten meal, corn steep liquor, dried yeast etc. as well as inorganic and organic nitrogen compounds such as ammonium salts (e.g. ammonium nitrate, ammonium sulfate, ammonium phosphate, etc.), urea, amino acid and the like.

The carbon and nitrogen sources need not be used in their pure form, because less pure material which contain traces of growth factors and considerable quantities of mineral nutrients, are also suitable for use. Further, there may be added to the medium mineral salts such as calcium carbonate, sodium or potassium phosphate magnesium salts and the like. If the culture medium is foamed remarkably, a defoaming agent such as liquid paraffin, higher alcohol, plant oil, mineral oil and silicones may be added.

Preferred production conditions of WF002 in massive amount may include a submerged aerobic cultural condition.

Preferred production conditions of WF002 in small amount may include a shaking or surface culture in flask or bottle.

In case where the production is carried out in a large tank, it is preferable to use the vegetative form of the organism for inoculation in the production tank in order to avoid growth lag.

Agitation and aeration of the culture broth may be accomplished in a variety of ways. Agitation are provided by a propeller or the similar mechanical agitation equipment, by revolving or shaking the fermentor, by various pumping equipment or by the passage of sterile air through the medium. The fermentation is usually conducted at a temperature between 20° C. and 35° C., preferably about 25° C. for 50 to 100 hours, which may be varied depending on the fermentation condition and scale.

Thus produced WF002 can be recovered from the cultured broth by conventional means which are commonly used for the recovery of other fermentation products such as antibiotics.

In general, most of the WF002 produced are found in the culture filtrate as well as in the cells of the cultured broth. The WF002 can be isolated from the filtrate and the cells of the cultured broth in a conventional manner such as concentration under reduced pressure, lyophilization, extraction with a solvent, pH adjustment, treatment with a resin (e.g. anion or cation exchange resin, non-ionic adsorption resin), treatment with an adsorbent (e.g. activated charcoal, silicic acid, silica gel, cellulose, alumina), crystallization, recrystallization and the like.

The WF002 have a strong antimicrobial activity against pathogenic microorganisms, especially pathogenic fungi such as, Aspergillus fumigatus, Candida albicans and the like. Accordingly, the WF002 is useful as an antimicrobial agent, especially antifungal agent which is used for the treatment of infectious diseases in human beings and animals.

As examples for showing such pharmacological effects of WF002, some pharmacological test data are illustrated in the followings.

Test 1 (Antimicrobial Activity)

Antimicrobial activity of WF002 was determined by a serial broth dilution method using 96-well microtiter plate in 100 µl of yeast nitrogen base dextrose medium. The inoculum was adjusted to $1 \times 10^5$ colony forming units/ml. Candida albicans and Aspergillus fumigatus were cultured at 37° C. for 24 hours and Cryptococcus neoformans was cultured at 37° C. for 48 hours in 5% $CO_2$ incubator. After incubation, the growth inhibition of microorganism in each well was determined by microscopic observation. The results were shown as MEC (minimum effective concentration: µg/ml) value (Table 2).

TABLE 2

| Antimicrobial activity of WF002. | |
|---|---|
| Microorganisms | MEC (µg/ml) |
| Candida albicans FP633 | 6.25 |
| Aspergillus fumigatus FP1305 | 0.04 |
| Cryptococcus neoformans YC203 | 50 |

The present antimicrobial agent comprising the WF002 is useful as a therapeutic agent for infectious diseases in animals including human beings.

The antimicrobial composition can be used in the form of pharmaceutical preparation, for example, in solid, semisolid or liquid form, which contains the WF002 in admixture with a pharmaceutical organic or inorganic carrier or excipient suitable for external, topical, enteral, parenteral, intravenous, intramuscular, or intramucous applications. The active ingredient may be compounded, for example, with usual non-toxic, pharmaceutically acceptable carriers for tablets, pellets, capsules, suppositories, solutions, emulsions, suspensions, ointments and any other form suitable for use. The pharmaceutically acceptable carriers are water, glucose, lactose, gum acacia, gelatin, mannitol, starch paste, magnesium trisilicate, talc, corn starch, keratin, colloidal silica, potato starch, urea and other carriers suitable for use in manufacturing preparations and in addition, auxiliary, stabilizing, thickening and coloring agents and perfumes. The antimicrobial compositions can also contain preserving or bacteriostatic agents thereby keeping the active ingredient in the desired preparations stable in activity. The active object compound is contained in the antimicrobial composition in an amount sufficient to produce the desired therapeutic effect upon the bacterially infected process or condition.

For applying this composition to human patients, it is preferably to apply it in a form of intraveneous, intramuscular, oral or percutaneous administration. While the dosage or therapeutically effective amount of the WF002 varies depending on the age, conditions of each individual patient to be treated, the preferred daily dosage of the WF002 can be selected from the range of 0.1–1000 mg/kg of the patient.

The following Example is given for the purpose of illustrating this invention, but not limited thereto.

BEST MODE OF CARRYING OUT OF THE INVENTION

Example (1) Fermentation of the Strain No.002 for the Production of WF002

An aqueous seed medium (160 ml) containing sucrose 2%, glycerol 2%, cottonseed meal 2%, dried yeast 1%, polypeptone 1%, $KH_2PO_4$ 0.1%, and Tween 80 0.1% was placed in each of three 500-ml Erlenmeyer flasks and was sterilized at 120° C. for 30 minutes. A loopful of the slant culture of the strain No.002 was inoculated in each of the seed flasks. The inoculated flasks were shaken on a rotary shaker (220 rpm, 5.1 cm throw) at 25° C. for 4 days, and 480 ml (three flasks) of the seed culture were inoculated to 20 liters of sterile production medium consisting of modified starch 4%, glucose 1%, cottonseed meal 1%, gluten meal 0.6%, corn steep liquor 3%, $(NH_4)_2SO_4$ 1%, $KH_2PO_4$ 1.2%, $Na_2HPO_4 \cdot 12H_2O$ 1.9%, β-cyclodextrin 1%, Adekanol LG-109 (defoaming agent, Asahi Denka Co., Ltd.) 0.05%, and Silicone KM-70 0.05% in a 30-liter jar fermentor. Fermentation was carried out at 25° C. for 4 days under aeration of 20 liters/minute and agitation of 200 rpm.

The production of the WF002 in the fermentation broth was monitored by HPLC analysis indicated below.

Analytical HPLC Condition column: YMC Pack ODS-AM 303, S-5 120A (250×4.6 mm I.D., YMC Co., Ltd.)

mobile phase: 45% aqueous acetonitrile containing 0.5% NaH$_2$PO$_4$.2H$_2$O flow rate: 1 ml/min.

detection: UV at 210 nm retention time: 8.0 min.

(2) Isolation and Purification of the WF002

The culture broth (100 liters) was extracted with an equal volume of acetone by stirring for 2 hours at room temperature. The mixture was filtered with an aid of diatomaceous earth. The filtrate was diluted with an equal volume of water and passed through a column (10 L) of DIAION HP-20 (non-ionic adsorption resin, Mitsubishi Chemical Co., Ltd.) packed with 25% aqueous acetone. The column was washed with 50% aqueous methanol (30 L) and then eluted with methanol (50 L). The active fraction (0–30 L) was diluted to 50 L with water and passed through a column (4 L) of YMC-GEL (ODS-AM 120-S50, YMC Co., Ltd.) packed with 50% aqueous methanol. The column was washed with 60% (12 L) and 70% (12 L) aqueous methanol and then eluted with 80% aqueous methanol (15 L). The active fraction (0–10 L) was diluted to 16 L with water and passed through a column (2 L) of YMC-GEL (ODS-AM 120-S50, YMC Co., Ltd.) packed with 50% aqueous methanol. The column was washed with 70% aqueous methanol (6 L) and eluted with 80% aqueous methanol (5.2 L). The active fraction (1–3.2 L) was concentrated under reduced pressure to dryness. The residue was dissolved in 50% aqueous methanol (2 L) and was subjected to column chromatography on YMC-GEL (ODS-AM 120-S50, YMC Co., Ltd. 2 L). The column was washed with 50% aqueous methanol (0.5 L) and 30% aqueous acetonitrile containing 0.5% NaH$_2$PO$_4$.2H$_2$O (6 L) and eluted with 40% aqueous acetonitrile containing 0.5% NaH$_2$PO$_4$.2H$_2$O (9 L). The active fraction (2–7 L) was diluted with an equal volume of water and passed through a column (2 L) of YMC-GEL (ODS-AM 120-S50, YMC Co., Ltd.) packed with 20% aqueous acetonitrile containing 0.25% NaH$_2$PO$_4$.2H$_2$O. The column was eluted with 40% aqueous acetonitrile containing 0.5% NaH$_2$PO$_4$.2H$_2$O (9.7 L). The active fraction (4.7–7.7 L) was diluted with an equal volume of water and passed through a column (2 L) of YMC-GEL (ODS-AM 120-S50, YMC Co., Ltd.) packed with 20% aqueous acetonitrile containing 0.25% NaH$_2$PO$_4$.2H$_2$O. The column was washed with 50% aqueous methanol (4 L) and 70% aqueous methanol (5 L) and eluted with 80% aqueous methanol (5.7 L). The active fraction (3–5.2 L) was concentrated in vacuo to give white precipitates. The precipitates were filtered and dried up to give 275 mg of the WF002 as white powder. This powder was dissolved in a small volume of methanol and further purified by preparative HPLC, using YMC-packed column (ODS-AM SH-343-5 AM S-5, 250×20 mm I.D., YMC Co., Ltd.) with 45% aqueous acetonitrile containing 0.5% NaH$_2$PO$_4$.2H$_2$O as a mobile phase and a flow rate of 9.9 ml/minute. Active fraction was diluted with an equal volume of water and passed through a column (2 L) of YMC-GEL (ODS-AM 120-S50, YMC Co., Ltd.) packed with 22.5% aqueous acetonitrile containing 0.25% NaH$_2$PO$_4$.2H$_2$O. The column was washed with 40% aqueous methanol (4 L) and then eluted with 75% aqueous methanol. The eluate was concentrated under reduced pressure to dryness. The residue was dissolved in a small volume of ethyl acetate and added with a large amount of n-hexane, and then was dried up to give 197 mg of WF002 as white powder.

What is claimed is:

1. A compound WF002 having the formula as follows:

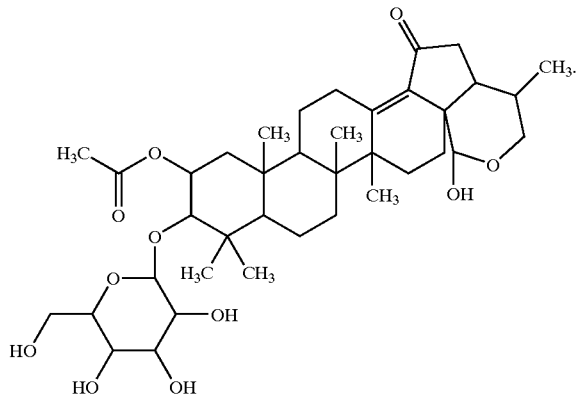

2. A compound of claim 1 having the following physicochemical properties a) Molecular weight: ES1:MS (negative): m/z 689 (M–H)

b) Elemental analysis: C, 61.08; H, 8.83 c) Melting point: 210–211° C.

d) Optical rotation: $[\alpha]_D^{23}$=+58° (c=0.5, methanol)

e) UV absorption spectrum: λ max($\xi$)=260 nm (methanol, 13000)

f) IR absorption spectrum: ν max(KBr)=3430, 2950, 2880, 1710, 1620, 1450, 1370, 1260, 1100, 1080, 1040 cm$^{-1}$ g) $^1$H-NMR spectrum: (500 MHZ, CD$_3$OD) δ(ppm): 5.11 (1H, m), 4.98 (1H, s), 4.37 (1H, d, J=8 Hz), 4.34 (1H, m), 4.08 (1H, m), 3.86 (1H, m), 3.67 (1H, m), 3.38 (1H, d, J=10 Hz), 3.32 (1H, m), 3.28–3.20 (3H, m), 3.13 (1H, m), 2.58 (1H, m), 2.28 (1H, m), 2.19 (1H, m), 2.06 (3H, s), 2.06 (3H, m), 1.81–1.5- (7H, m), 1.49–1.20 (4H, m), 1.22 (3H, d, J=8 Hz), 1.20 (3H, s), 1.13 (3H, s), 1.12 (1H, m), 0.98 (3H, s), 0.97 (1H, m), 0.93 (3H, s), 0.92 (3H, s), h) $^{13}$C-NMR spectrum: (125 MHZ, CD$_3$OD) δ(ppm): 211.3 (s), 173.2 (s), 157.3 (s), 136.9 (s), 105.9 (s), 95.2 (d), 95.2 (d), 89.3 (d), 78.3 (d), 77.8 (d), 75.9 (d), 71.9 (d), 71.7 (d), 63.0 (t), 59.4 (t), 56.4 (d), 52.7 (d), 45.94 (d), 45.90 (t), 45.2 (s), 44.9 (s), 44.4 (t), 44.1 (s), 42.1 (s), 39.5 (s), 35.6 (t), 35.0 (t), 31.3 (d), 30.1 (t), 28.7 (q), 28.1 (a), 24.9 (t), 23.0 (t), 21.7 (q), 21.1 (q), 19.4 (q), 19.2 (t), 18.3 (q), 17.9 (q), i) Solubility Soluble: methanol, ethyl acetate, dimethylsulfoxide Insoluble: water, n-hexane, j) Color reaction Positive: reactions with iodine vapor and cerium sulfate, and Molisch's test, respectively, Negative: reactions with ninhydrin, Ehrlich's reagent, Dragendorff reagent and ferric chloride, respectively.

3. A process for the preparation of the compound WF002 of claim 1 which comprises culturing a compound WF002-producing microorganism in a nutrient medium and recovering the compound WF002 from the resultant cultured broth.

4. An antimicrobial agent comprising the compound of claim 1 and a carrier.

5. A pharmaceutical composition comprising an antimicrobial effective amount of the compound of claim 1 and a pharmaceutically acceptable carrier.

6. A method of killing microorganisms which comprises applying the compound of claim 1 to the microorganism.

7. A method of killing fungi which comprises applying the compound of claim 1 to the fungi.

8. A method of treating an infectious disease caused by a pathogenic microorganism comprising applying the compound of claim 1 to said pathogenic microorganism.

9. An isolated culture of *Myrothecium cinctum* No. 002.

10. A process for the preparation of *Myrothecium cinctum* No. 002 comprising culturing a *Myrothecium cinctum* No. 002-producing microorganism in a nutrient medium and recovering *Myrothecium cinctum* No. 002 from the resultant cultured broth.

\* \* \* \* \*